United States Patent

Cabot

(10) Patent No.: US 8,808,246 B2
(45) Date of Patent: Aug. 19, 2014

(54) PERIPHERAL BLOOD SAMPLING METHODS AND DEVICES

(75) Inventor: Michael S. Cabot, Littleton, MA (US)

(73) Assignee: The General Hospital Corporation, Boston, MA (US)

( * ) Notice: Subject to any disclaimer, the term of this patent is extended or adjusted under 35 U.S.C. 154(b) by 318 days.

(21) Appl. No.: 13/386,133

(22) PCT Filed: Jul. 20, 2010

(86) PCT No.: PCT/US2010/042635
§ 371 (c)(1),
(2), (4) Date: Apr. 11, 2012

(87) PCT Pub. No.: WO2011/011436
PCT Pub. Date: Jan. 27, 2011

(65) Prior Publication Data
US 2012/0191010 A1  Jul. 26, 2012

Related U.S. Application Data

(60) Provisional application No. 61/227,321, filed on Jul. 21, 2009.

(51) Int. Cl.
*A61M 5/32* (2006.01)

(52) U.S. Cl.
USPC ....... 604/163; 600/585; 604/508; 604/164.04

(58) Field of Classification Search
CPC .................. A61M 2039/062; A61M 25/0021; A61M 25/04
USPC ...................... 600/585; 604/164.04, 508, 163
See application file for complete search history.

(56) References Cited

U.S. PATENT DOCUMENTS

| 4,192,319 A | 3/1980 | Hargens et al. |
| 4,808,158 A | 2/1989 | Kreuzer et al. |
| 5,147,334 A | 9/1992 | Moss |
| 5,201,722 A | 4/1993 | Moorehead et al. |
| 5,203,771 A | 4/1993 | Melker et al. |

(Continued)

FOREIGN PATENT DOCUMENTS

WO    2011/011436 A2    1/2011

OTHER PUBLICATIONS

International Preliminary Report on Patentability from PCT/US10/042635, dated Feb. 2, 2012.

(Continued)

*Primary Examiner* — Max Hindenburg
*Assistant Examiner* — Renee Danega
(74) *Attorney, Agent, or Firm* — Nutter McClennen & Fish LLP

(57) ABSTRACT

Methods and devices are provided for transporting fluid between a body and an external source. More particularly, the methods and devices provided can be used to transport blood from a body. In one exemplary embodiment, a system is provided for transporting fluid between a body and an external source. The system can include a collection catheter that is sized to fit inside a catheter that is placed in the body and configured to have its distal end extend beyond a distal end of the catheter that is placed in the body. Various methods for transporting fluid from the body to an external source are also provided.

9 Claims, 6 Drawing Sheets

(56) References Cited

U.S. PATENT DOCUMENTS

| | | | |
|---|---|---|---|
| 5,360,407 | A | 11/1994 | Leonard et al. |
| 5,562,631 | A | 10/1996 | Bogert |
| 5,611,782 | A | 3/1997 | Haedt |
| D384,741 | S | 10/1997 | Musgrave et al. |
| 5,749,857 | A | 5/1998 | Cuppy |
| 5,755,709 | A | 5/1998 | Cuppy |
| 5,827,229 | A * | 10/1998 | Auth et al. ............. 604/171 |
| 5,853,393 | A | 12/1998 | Bogert |
| 5,944,695 | A | 8/1999 | Johnson et al. |
| 6,080,138 | A | 6/2000 | Lemke et al. |
| 6,197,001 | B1 | 3/2001 | Wilson et al. |
| 6,508,790 | B1 * | 1/2003 | Lawrence ............ 604/167.05 |
| 6,692,473 | B2 | 2/2004 | St. Cyr et al. |
| 6,719,726 | B2 | 4/2004 | Meng et al. |
| 6,719,781 | B1 | 4/2004 | Kim |
| 6,908,459 | B2 | 6/2005 | Harding et al. |
| 7,135,008 | B2 | 11/2006 | O'Mahony et al. |
| 7,252,654 | B2 | 8/2007 | VanTassel et al. |
| 7,311,689 | B2 | 12/2007 | Levin et al. |
| 7,462,161 | B2 | 12/2008 | O'Mahony et al. |
| 7,615,033 | B2 | 11/2009 | Leong |
| 7,670,320 | B2 | 3/2010 | Iwase et al. |
| 7,691,088 | B2 | 4/2010 | Howell |
| 7,713,250 | B2 | 5/2010 | Harding et al. |
| 7,717,882 | B2 | 5/2010 | Harding |
| 7,762,977 | B2 | 7/2010 | Porter et al. |
| 7,766,961 | B2 | 8/2010 | Patel et al. |
| 7,771,394 | B2 | 8/2010 | Shue et al. |
| 8,366,685 | B2 | 2/2013 | Devgon |
| 2002/0120215 | A1 | 8/2002 | Crawford et al. |
| 2004/0138622 | A1 | 7/2004 | Palasis |
| 2004/0181192 | A1 | 9/2004 | Cuppy |
| 2007/0219460 | A1 | 9/2007 | Goldenberg |
| 2007/0282280 | A1 | 12/2007 | Tennican |
| 2008/0033396 | A1 * | 2/2008 | Danek et al. ................ 604/508 |
| 2008/0045862 | A1 | 2/2008 | Dalebout et al. |
| 2009/0156963 | A1 | 6/2009 | Noble et al. |
| 2010/0286657 | A1 | 11/2010 | Heck |
| 2010/0305519 | A1 | 12/2010 | McKinnon et al. |

OTHER PUBLICATIONS

International Search Report and Written Opinion from PCT/US10/042635, dated Feb. 25, 2011.

[No author listed] "Blood Sampling Hemolysis Study for the MaxPiusTM Positive Flow Connector," Maximus Medical Products, Inc. © 2003, 1 pg.

[No author listed] "Connect and Protect with BD Diagnostics—Preanalytical Systems," BD Vacutainer®, Luer-LokTM, Access Device, 2 pgs. 2006.

[No author listed] "Evidence-Based Practice (EBP) Guideline Drawing Labs from Peripheral IV Sites," Nursing Research Council of United Hospital—Developed Apr. 2004; Revised Mar. 2009, 3 pgs.

[No author listed] "Needleless IV Access Devices," BD Q-SyteTM, Luer Access Split-Septum, 2007, 1 pg.

[No author listed] "Vascular Access Procedures," Vascular Access Procedures, [retrieved on Mar. 16, 2011] Retrieved from the Internet <URL: http://www.radiologyinfo.org/en/info.cfm?pg=vasc_access> 7 pgs. 2011.

[No author listed] WHO guidelines on drawing blood: best practices in phlebotomy, © World Health Organization 2010 125 pgs.

Cox et al., Blood samples drawn from IV catheters have less hemolysis when 5-mL (vs 10-mL) collection tubes are used. J Emerg Nurs. Dec. 2004;30(6):529-33.

Frey, "Drawing Blood Samples From Vascular Access Devices: Evidence-based Practice," Journal of Infusion Nursing: Sep./Oct. 2003, vol. 26, Issue 5, pp. 285-293, Article: CE, Abstract.

Himberger et al., Accuracy of drawing blood through infusing intravenous lines. Heart Lung. Jan.-Feb. 2001;30(1):66-73. Abstract.

Jagger, et al., Drawing Venous Blood With Syringes: A Risky Use of Injection Equipment,: Advances in Exp Prev. 2000;5(3):3 pgs.

* cited by examiner

PERIPHERAL BLOOD SAMPLING METHODS AND DEVICES

CROSS-REFERENCE TO RELATED APPLICATIONS

The present application claims priority to U.S. Provisional Application No. 61/227,321, filed on Jul. 21, 2009 and entitled "Peripheral Blood Sampling Methods and Devices," which is hereby incorporated by reference in its entirety.

TECHNICAL FIELD

The present invention generally relates to devices and methods for transporting fluid to and from the body, and more particularly relates to devices and methods for taking blood samples from a body.

BACKGROUND

Fluid, particularly blood, is drawn from patients on a routine basis in many hospitals and laboratories. One of the most common ways to draw blood is venipuncture, which is a method that involves inserting a needle through the skin and into an underlying vein. In some instances blood can be drawn as frequently as every six hours. Further, patients can be subjected to multiple attempts each time a needle is inserted into the skin, and the more frequent the withdrawals become, the more difficult it can become to find a location for the next withdrawal. Each attempt can be painful and a nuisance. Other options for the withdrawal of blood and other fluids, however, are limited, and can often be even more painful than venipuncture. Some of these options include the use of Peripherally Inserted Central Catheters (PICC lines), central lines, repeated peripheral venipuncture, and groin sticks.

Current guidelines allow blood to be drawn off a peripheral intravenous catheter at the time of insertion. Studies show that blood sampled from a peripheral intravenous catheter yields results similar to those obtained by venipuncture. Clots, however, tend to form at the tip of an intravenous catheter, so it is generally not desirable to draw blood from peripheral intravenous catheters as they are currently designed. The clots can be both dangerous and painful. Further, as blood is drawn from peripheral intravenous catheters, the tip of the intravenous catheters can become damaged. A damaged intravenous catheter tip can lead to compromised blood samples and undesirable harm or damage to the instrumentation and the patient.

Accordingly, it is desirable to have devices and methods that allow for less painful and more dependable blood sampling and fluid removal from a patient. It is also desirable to have devices and methods that allows for multiple samples to be taken over a period of time from the same puncture site.

SUMMARY

Methods and devices are generally provided for transporting fluid between a body and an external source. In one aspect, a system for transporting fluid between a body and an external source can include a catheter having proximal and distal ends. The catheter can be configured to fit inside a conduit disposed in a body. The catheter can also be configured to allow the distal end of the catheter to extend beyond a distal end of the conduit disposed in the body. Still further, the catheter can be configured to allow the proximal end of the catheter to couple to an external source so that a fluid can be transported between the external source and the body. Typically blood can be drawn from the distal end of the catheter, through the catheter, and out of the proximal end of the catheter to the external source. Two examples of an external source include a Vacutainer® blood collection tube, marketed by BD, and a syringe. The system can also include an external catheter adapter, which can be designed to couple to the proximal end of the catheter to assist with communication between the catheter and the external source. In one embodiment the external source adapter can include a tube having a distal end coupled to the proximal end of the catheter and a proximal end configured to couple to an external source. The external source adapter can also include a valve configured to open and close a pathway of the tube. Still further, the external source adapter can include a connector coupled to the distal end of the tube and configured to couple to a conduit disposed in a body. Alternatively, or additionally, the connector can be configured to couple to the catheter to facilitate the coupling of the external source adapter to the catheter.

A second adapter, a conduit device adapter, can also be included in the system for transporting a fluid between a body and an external source. The conduit device adapter can be designed to couple to the proximal end of a conduit disposed in a body to assist with communication between the catheter disposed in the conduit and the tube of the external source adapter. In one embodiment the conduit device adapter can include a device adapting tube having a distal end configured to couple to a conduit disposed in a body and a proximal end configured to couple to the distal end of the tube of the external source adapter. The conduit device adapter can also include a device adapting valve configured to open and close a pathway of the device adapting tube. Further, the conduit device adapter can include a device adapting connector coupled to the distal end of the device adapting tube. The device adapting connector can be configured to couple to a conduit disposed in a body. In an exemplary embodiment that includes both an external source adapter and a conduit device adapter, the connector of the external source adapter can be coupled to the distal end of the tube and can be configured to couple to the proximal end of the device adapting tube and/or the collection catheter rather than a conduit disposed in a body and/or the collection catheter. Further, in one embodiment the system can include a second catheter such that the second catheter is the conduit disposed in the body.

In another embodiment, a protective sheath is provided and can extend between the proximal end of the catheter and a catheter connector. The protective sheath can be movable between an expanded configuration in which the catheter is substantially enclosed by the protective sheath and a contracted configuration in which only a proximal portion of the catheter is enclosed by the protective sheath and the distal end of the catheter extends a distance beyond a distal end of a conduit. The catheter connector can be configured to couple to a conduit connector disposed on a proximal end of a conduit. In other embodiments, the protective sheath can include a latch mechanism configured to retain the protective sheath in the contracted configuration when actuated. The catheter can optionally be permanently coupled to a conduit disposed within a body.

In another aspect, a method for transporting a fluid between a body and an external source is provided. For example, a catheter can be inserted into a placed catheter that is disposed in a body. The catheter, sometimes referred to as a collection catheter, can be inserted into the placed catheter and beyond a distal end of the placed catheter. The collection catheter can also be coupled to an external source. The external source can be used to transport fluid between the body and the external source through the collection catheter. In one exemplary embodiment, blood is drawn from the body, through the collection catheter, and into the external source. Two examples of an external source include a Vacutainer® blood collection tube marketed by BD and a syringe.

An exemplary method can also include using one or more adapters to assist in connecting the collection catheter to the placed catheter and/or to assist in connecting an external source to the collection catheter. In one embodiment, the method can include attaching an external source adapter to a proximal end of the catheter and attaching a placed catheter adapter to a proximal end of the placed catheter. The external source adapter can include a tube having a distal end coupled to the proximal end of the catheter and a proximal end that is configured to couple to the external source. The external source adapter can also include an external source adapter valve that is configured to open and close a pathway of the tube of the external source adapter. The placed catheter adapter can include a tube having a distal end coupled to the proximal end of the placed catheter and a proximal end coupled to the distal end of the external source adapter. The placed catheter adapter can also include a placed catheter adapter valve configured to open and close a pathway of the tube of the placed catheter adapter. Prior to inserting the collection catheter into the placed catheter, the placed catheter adapter valve can be opened and the external source adapter valve can be closed. After the external source is coupled to the collection catheter, the external source adapter valve can be opened. After the external source is used to facilitate transporting fluid between the body and the external source through the catheter, the collection catheter can be removed from the placed catheter, the placed catheter valve can be closed, and the external source adapter can be removed. Other external source adapters and/or collection catheters can be used with the placed catheter adapter and the placed catheter. In one exemplary embodiment, prior to inserting the collection catheter, the placed catheter can be cleared of any materials disposed therein, for example by flushing the placed catheter with a sterile solution or suctioning out any air disposed therein.

In another exemplary method, inserting a catheter into a proximal portion of a placed catheter disposed in a body and beyond a distal end of the placed catheter can include moving a proximal end of a substantially flexible protective sheath toward a distal end thereof to cause the protective sheath to contract and move the catheter through the placed catheter and beyond the distal end of the placed catheter. The method can further include latching the distal end of the protective sheath to the proximal end of the protective sheath to retain the catheter within the placed catheter, unlatching the distal end of the protective sheath from the proximal end of the protective sheath after an external source is used to facilitate transporting fluid between the body and the external source through the catheter, and expanding the protective sheath to withdraw the catheter from within the place catheter.

In a further aspect, a kit for transporting a fluid between a body and an external source is provided and can include two catheters. The first catheter can have proximal and distal ends and the second catheter can have proximal and distal ends and a diameter that is smaller than a diameter of the first catheter. The second catheter can be configured to allow its distal end to be positioned beyond the distal end of the first catheter. The kit can also include a locking mechanism for coupling the first and second catheter together. In one embodiment the locking mechanism can include a tube having a distal end that is configured to be coupled to the first catheter, a proximal end that is configured to receive an external source, and a pathway disposed between the proximal and distal ends. The locking mechanism can further include a valve that is configured to open and close the pathway of the tube. The kit can also include one or more adapters, in which case the proximal end of the tube can be configured to receive one of the adapters. The adapter can include an adapter tube having a distal end that is configured to be coupled to the proximal end of the second catheter and the proximal end of the tube, a proximal end that is configured to receive an external source, and a pathway disposed between the proximal and distal ends. The adapter can further include an adapter valve that is configured to open and close the pathway of the adapter tube.

In another aspect, a kit for transporting a fluid between a body and an external source is provided and can include a catheter and at least one adapter. In an exemplary embodiment two adapters are provided. The catheter can have proximal and distal ends and can be configured to both fit inside a conduit disposed in a body and extend such that the distal end of the catheter extends beyond a distal end of the conduit disposed in the body. The first adapter can include a first adapter tube that has a distal end configured to couple to the proximal end of the catheter and a proximal end configured to couple to an external source, as well as a first adapter valve that is configured to open and close a pathway of the first adapter tube. The second adapter can include a second adapter tube that has a distal end configured to couple to a conduit disposed in a body and a proximal end configured to couple to the distal end of the first adapter tube, as well as a second adapter valve that is configured to open and close a pathway of the second adapter tube. In one embodiment the kit can also include a second catheter such that the second catheter is the conduit disposed in the body.

In another embodiment, a substantially flexible protective sheath can extend between the proximal end of the second catheter and the locking mechanism and can be configured to enclose and protect at least a portion of the second catheter. In some embodiments, the protective sheath can be configurable between a first, expanded length and a second, contracted length, and a latch mechanism can be disposed on the protective sheath and configured to retain the protective sheath in the second, contracted length. The protective sheath can be configured to be in the second, contracted length when the distal end of the second catheter is positioned beyond the distal end of the first catheter.

In a further aspect, a kit for transporting a fluid between a body and an external source is provided and can include a catheter system having a catheter with proximal and distal ends and can be configured to fit inside a conduit disposed in a body and extend such that the distal end extends beyond a distal end of the conduit disposed in the body. The catheter system can also include a proximal catheter connector and a distal catheter connector, the distal catheter connector being configured to couple to an external source. The catheter system can further include a substantially flexible protective sheath extending between the proximal and distal catheter connectors and disposed around at least a portion of the catheter.

In some embodiments, the kit can also include a conduit system having a substantially tubular conduit with proximal and distal ends and can be configured to form a pathway into the body and to receive the catheter therein. The conduit system can also include a proximal conduit connector disposed on the proximal end of the conduit and configured to couple to the distal catheter connector. The catheter system can further include a latch mechanism having a first latch component disposed on a proximal end of the protective sheath and a second latch component disposed on the distal end of the protective sheath. In some embodiments, the flexible sheath can be configured to collapse to a reduce length configuration such that the first latch component and the second latch component can be latched together when the catheter is disposed within the conduit such that the distal end extends beyond the distal end of the conduit.

DETAILED DESCRIPTION

Figure 1:
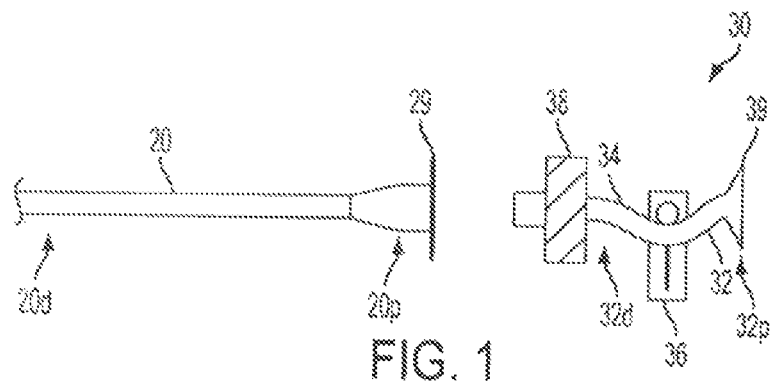
FIG. 1 is a side view of one embodiment of a placed catheter adapter.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

While the devices and methods described in this application are generally discussed with respect to drawing a blood sample from a body, the devices and methods can also be used to draw other fluids from a body. Likewise, although the devices and methods described in this application are generally discussed with respect to drawing samples out of a body, the devices and methods can also be used to inject fluid into a body. The body can be any body, although preferably the body is a human body. The devices and procedures can be used in a body of any age as well, although the sizes of the components will likely change depending on the size of the body. For example, the components for drawing blood will likely be smaller for a child or infant than an adult because the vein from which the blood is drawn is smaller. The devices and methods described herein are generally used for intravenous procedures, and are particularly well suited for use with veins in the arm and hand. The devices and methods, however, can be applied to other locations in a body. Because the devices described herein can have a variety of components that selectively couple, a person skilled in the art will recognize that a variety of different connectors, whether mechanical, electrical, or otherwise, can be used to couple various components together. Further, to the extent that connectors are described as having male and female components, for example mechanical Luer lock connectors with female hubs and male locks, a person skilled in the art will recognize that the male and female components can be interchangeably located on the respective components.

In one exemplary embodiment of a device for transporting fluid between a body and an external source, a system and/or kit, is provided that includes a first conduit configured to fit within a second conduit. The second conduit can have a distal end that is configured to be placed near a location from which blood is to be drawn from a body and a proximal end located outside of the body. In some embodiments the second conduit can be part of the system and/or kit, while in other embodiments the second conduit can be separately provided. The first conduit can be configured to fit inside the second conduit, and further, can be configured to have its distal end extend beyond the distal end of the second conduit. In one embodiment a locking mechanism can be used to couple the first and second conduits. A proximal end of the first conduit can be configured to be coupled to an external source that is configured to facilitate the removal of blood from the body, through the first conduit, and to the external source, as discussed in further detail below. For ease of reference, the first conduit will generally be referred to as the collection catheter and the second conduit as the placed catheter.

Figure 4A:
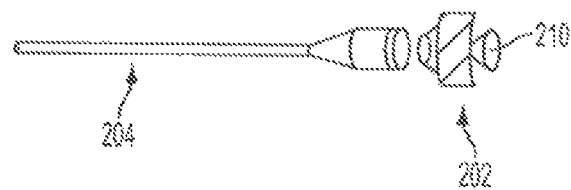
FIG. 4A is a side view of an exemplary straight IV with a resealable membrane.
Figure 4B:
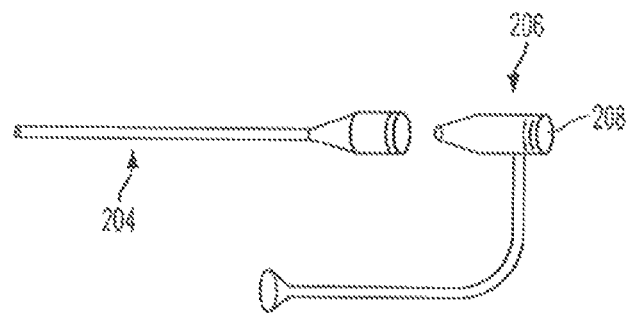
FIG. 4B is a side view of an exemplary straight IV with a saline lock.
Figure 4C:
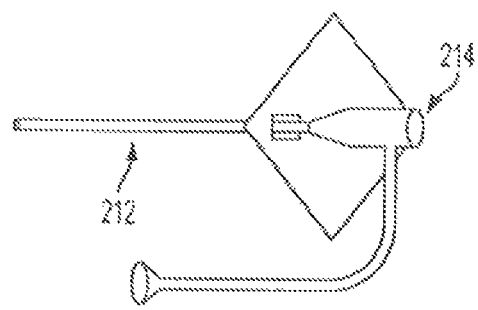
FIG. 4C is a side view of an exemplary butterfly-type IV.

The first conduit and/or placed catheter can generally be any IV system known in the art that is configured to be disposed within the body and to be repeatedly accessed. For example, as shown in FIG. 4A, the collection catheter can be a straight-style IV catheter 200 with an adapter 202 having a pierceable, resealable membrane 210 that can be configured to be pierced by a needle prior to receiving a collection catheter. Another embodiment is shown in FIG. 4B in which a straight-style IV catheter 204 is provided with a saline lock 206 having a pierceable, resealable membrane 208 that can also be pierced with a needle prior to receiving a collection catheter. The saline lock 206 can allow the placed catheter 204 to be flushed with saline for cleaning after use by the collection catheter, as will be addressed in more detail below. A further embodiment is shown in FIG. 4C in which a butterfly-type IV 212 is provided having a pierceable, resealable silicone rubber stopper 214, also configured to be pierced by a needle prior to receiving a collection catheter. As will be appreciated by those skilled in the art, there are many various possible IVs known in the art that can be used as the placed catheter and any one of them can be used in any of the embodiments described herein.

In any of the embodiments disclosed herein, each of the collection catheter and the placed catheter can have a variety of shapes and sizes, but generally the collection catheter should fit within the placed catheter and extend a distance beyond a distal end of the placed catheter. This allows a fluid sample (e.g., blood) to be taken directly from the source (e.g., vein) and avoids the pain and clotting issues addressed above. Because the collection catheter must extend through the placed catheter and beyond a distal end of the placed catheter, it is generally desirable for the collection catheter and the placed catheter to have a similar shape. In one embodiment each of the collection catheter and the placed catheter can be substantially tubular. Further, while each of the collection catheter and the placed catheter can have different sizes, the collection catheter typically is longer than the placed catheter. In some embodiments a length of the placed catheter can be in a range of about 1 cm to about 10 cm, in a range of about 1.4 cm to about 5 cm, for example, about 3 cm. In other embodiments a length of the collection catheter can be in a range of about 1.5 cm to about 16 cm, in a range of about 6 cm to about 11 cm, for example, about 7.5 cm. However, so long as a distal portion of the collection catheter extends beyond a distal end of the placed catheter, the collection catheter can be any length, including shorter than the placed catheter. While the distance that the distal end of the collection catheter extends beyond the distal end of the placed catheter can vary, in some embodiments the distal end of the collection catheter extends beyond the distal end of the placed catheter a distance in a range of about 0.1 cm to about 3 cm, in a range of about 0.5 cm to about 1.5 cm, for example, about 1 cm.

In embodiments where the first and second conduits are catheters, such as the illustrated embodiments of FIGS. 1-7, catheters sized by gauge number can be used to help determine the appropriate relationship between the diameter of the placed catheter and the diameter of the collection catheter. For example, in one embodiment the placed catheter can be a standard intravenous 20 gauge catheter while the collection catheter can be one or two sizes smaller, such as a 21 or 22 gauge catheter. A person skilled in the art will recognize that higher gauge numbers typically indicate catheters having a smaller diameter. Any sized catheter can be used in the disclosed devices and methods, although typically catheters for use in adults range from approximately 14 to 22 gauge and catheters for use in children, infants, and sometimes elderly adults range from approximately 20 to 24 gauge. Further, to the extent that other catheters or conduits that do not have particular gauges are used, or to the extent that gauge standardization changes, so long as the collection catheter has a diameter that is smaller than the diameter of the placed catheter and a length that allows the distal end of the collection catheter to extend beyond the distal end of the placed catheter, a person skilled in the art will easily be able to incorporate these other catheters or conduits into the devices and methods disclosed herein. It is generally desirable to select a diameter for the collection catheter that is as close to the diameter of the placed catheter as possible while still allowing for the collection catheter to easily slide through the placed catheter.

Any of the placed catheters and the collection catheters disclosed herein can likewise be made from a variety of materials. While the materials used to make the placed catheter and the collection catheter can be the same, they can also be different. It can be desirable to select materials that allow the collection catheter to easily slide through the placed catheter. Some examples of materials that can be used to form the placed catheter and the collection catheter include silicone, Teflon, rubber, polyurethane, and resilient polymeric materials such as a fluorinated ethylene propylene polymer. In one exemplary embodiment both the placed catheter and the collection catheter are made of fluorinated ethylene propylene polymer.

An exemplary system and/or kit can also include one or more assemblies or adapters that are configured to assist with the placement of the collection catheter in the placed catheter and/or assist with connecting the collection catheter with an external source. In one embodiment any type of locking mechanism can be used to couple the placed and collection catheters to each other. For example, a mechanical connector can be used to couple a proximal end of the placed catheter to a proximal end of the collection catheter.

Figure 2:
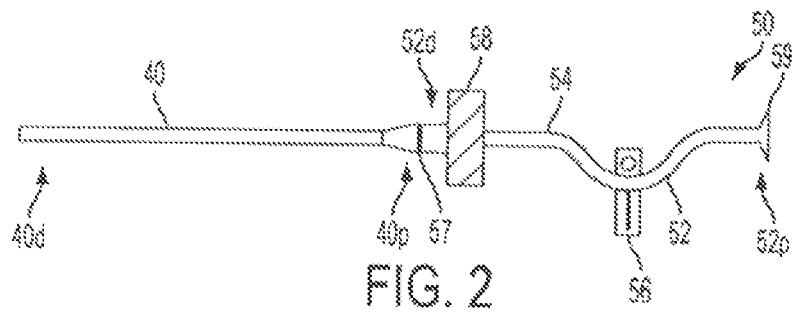
FIG. 2 is a side view of one embodiment of an external source adapter.

FIGS. 1 and 2 illustrate one embodiment that includes a placed catheter 20 and a collection catheter 40. As shown in FIG. 1, a first adapter, a placed catheter adapter 30, is configured to attach to a proximal end 20p of the placed catheter 20. The placed catheter adapter 30 is sometimes referred to as a conduit device adapter, among other names. The placed catheter adapter 30 can include a tube 32 forming a pathway 34 and a valve, coupled to the tube 32 and configured to open and close the pathway 34. The placed catheter adapter 30 can generally be configured to allow the collection catheter 40 to be inserted through the placed catheter adapter 30 and into the placed catheter 20 such that the collection catheter 40 can be removable and replaceable. More particularly, a distal end of the tube 32d of the placed catheter adapter 30 can be configured to couple to the placed catheter 20 and a proximal end 32p of the tube 32 can be configured to couple to a proximal end 40p of the collection catheter 40.

Similar to the shape and size of the placed catheter 20 and the collection catheter 40, the tube 32 can be a variety of shapes and sizes, although it is generally shaped and sized to receive a collection catheter and fit with a placed catheter to prevent leakage of fluid therebetween. In one exemplary embodiment a diameter of the tube 32 is approximately in the range of about 1 to 2 millimeters and a length of the tube 32 is kept relatively small, approximately in the range of about 2 to 10 centimeters. Keeping the length of the tube 32 of the placed catheter adapter 30 small provides less tubing in which the collection catheter 40 can get tangled or stuck, and further, keeps the tube 32 out of the way when the placed catheter adapter 30 is coupled to the placed catheter 20 for an extended period of time. The diameter of the tube 32 is generally sized to be large enough to receive the collection catheter 40, but not much larger than the collection catheter 40 so as not to create unwanted space therebetween. In an exemplary embodiment the diameter of the tube 32 is the same as the diameter of the placed catheter 20. Also similar to the placed catheter 20 and the collection catheter 40, the tube 32 can be made of a variety of different materials, including many of the same materials that can be used to form the placed and collection catheters 20, 40, respectively. It is generally preferred that the tube 32 be flexible. In one exemplary embodiment the tube 32 is made of silicone.

The valve of the placed catheter adapter 30 can be a variety of devices that are capable of closing and opening the pathway 34 of the tube 32. In the illustrated embodiment the valve is a clamp 36 that can close the pathway 34 by pinching the tube 32. Generally, when inserting the collection catheter 40 through the tube 32, the valve 36 is configured to keep the pathway 34 open so that the collection catheter 40 can pass through the tube 32 and into the placed catheter 20. The valve can also help to prevent blood from dripping when the collection catheter 40 is inserted into the placed catheter adapter 30. It is generally desirable to keep the clamp 36 open whenever the collection catheter 40 is disposed in the tube 32 because pinching the collection catheter 40 by closing the clamp 36 can damage the collection catheter 40. When no catheter or other object is inserted in the tube 32, it is generally desirable to keep the clamp 36 closed so that the body can be closed from an outside environment.

The placed catheter adapter 30 can also include a connector that is configured to assist in coupling the placed catheter adapter 30 with the proximal end 20p of the placed catheter 20. In the illustrated embodiment the proximal end 20p of the placed catheter 20 is a female hub 29 and the connector is a male Luer lock 38 configured to couple to the female hub 29 of the placed catheter 20. While Luer locks are often used for intravenous procedures, other connectors can also be incorporated into the design of the placed catheter 20 and the placed catheter adapter 30.

The proximal end 32p of the tube 32 of the placed catheter adapter 30 can be configured to receive a number of different devices. In the illustrated embodiment the proximal end 32p of the tube 32 has a female Luer lock hub 39. The female Luer lock hub 39 allows the proximal end 32p of the tube 32 to receive a male Luer lock of a second adapter and a device for clearing the tube 32 of the placed catheter adapter 30 and the placed catheter 20 of any undesirable material, such as fluid, disposed therein, for instance by flushing a solution through the tube 32 and the placed catheter 20. Two examples of devices for flushing include an intravenous infusion device and a syringe. It is generally desirable to clear the placed catheter 20 of any undesirable material prior to attaching a second adapter or inserting a collection catheter into the placed catheter 20. The solution can be any sterile solution, although preferably it is an iso-osmotic solution, such as saline. Further, gases, such as air, can be removed from the tube 32 of the placed catheter adapter 30 and the placed catheter 20 as well. In one exemplary embodiment this is accomplished by coupling the female Luer lock hub 39 of the placed catheter adapter 30, which can be configured to receive other devices in addition to a device for flushing, with a device for suctioning fluid and/or gases, such as air, from the tube 32 and the placed catheter 20. Two examples of devices for suctioning, a Vacutainer® blood collection tube marketed by BD and a syringe, are discussed in more detail below.

FIG. 2 illustrates a second adapter, an external source adapter 50, that is configured to attach to a proximal end 40p of the collection catheter 40 and receive an external source at a distal end thereof. The external source adapter 50 can have many of the same features of the placed catheter adapter 30. For example, it can include a tube 52 forming a pathway 54 and a valve, coupled to the tube 52 and configured to open and close the pathway 54. The external source adapter 50 can generally be configured to allow an external source to communicate through the collection catheter 40 to a portion of the body from which blood is being removed so that the external source can facilitate the removal of blood from the body to the external source. More particularly, a proximal end 52p of the tube 52 of the external source adapter 50 can be configured to couple to an external source and a distal end 52d of the tube 52 can be configured to couple to at least one of the collection catheter 40 and the proximal end 32p of the placed catheter adapter 30, as discussed in further detail below.

The tube 52 can be a variety of shapes and sizes, although it is generally shaped and sized to allow blood to flow through the tube 52, from the collection catheter 40, and to the external source. When comparing the size of the tube 52 of the external source adapter 50 to the tube 32 of the placed catheter adapter 30, a length of the tube 52 of the external source adapter 50 can typically be longer. This is because a longer tube 52 allows an operator more room to work. Further, some of the benefits of a shorter tube, such as not getting in the way, are not as important for the external source adapter 50 because typically the external source adapter 50 is not left in place for extended periods of time like the placed catheter adapter 30 can be. The diameter of the tube 52 of the external source adapter 50 can be approximately the same diameter as the diameter of the collection catheter 40 to facilitate any easy connection therebetween, although it does not have to be. In one exemplary embodiment the length of the tube 52 of the external source adapter 50 is approximately in the range of about 5 to 25 centimeters and the diameter is approximately in the range of about 0.8 to 2 millimeters. Further, the tube 52 of the external source adapter 50 can be made of a variety of different materials, including many of the same materials that can be used to form the placed catheter 20, the collection catheter 40, and the tube 32 of the placed catheter adapter 30. Preferably the tube 52 is flexible. In one exemplary embodiment the tube 52 of the external source adapter 50 is made of silicone.

Similar to the valve of the placed catheter adapter 30, the valve of the external source adapter 50 can be a variety of devices that are capable of closing and opening the pathway 54 of the tube 52. In the illustrated embodiment the valve is a clamp 56 that can close the pathway 54 by pinching the tube 52. Generally, when an external source is connected to the proximal end 52p of the tube 52 and is being operated, the clamp 56 is configured to keep the pathway 54 open so that fluid can pass through the tube 52 toward the external source. When no external source is connected to the proximal end 52p of the tube 52, or even when the external source is not being operated, the clamp 56 can be in the closed position so that the body can be closed from an outside environment.

The connection between the proximal end 40p of the collection catheter 40 and the distal end 52d of the tube 52 of the external source adapter 50 can be achieved in a variety of different ways using a variety of different mechanisms. For example, the external source adapter 50 can include a connector that is configured to mate to either the proximal end 40p of the collection catheter 40 or a proximal end of the placed catheter adapter 30. In the illustrated embodiment, the proximal end 40p of the collection catheter 40 is coupled to the proximal end 52p of the tube 52 of the external source adapter 50 to create a single assembly that can be coupled to the placed catheter adapter 30. One way such an assembly can be formed is by jamming the proximal end 40p of the collection catheter 40 into the distal end 52d of the tube 52 of the external source adapter 50. The proximal end 32p of the tube 32 of the placed catheter adapter 30, which can include the female hub 39, and a connector, which can be a male Luer lock 58 disposed on the external source adapter 50 and configured to screw onto the female hub 39 of the placed catheter adapter, can be coupled together so that the assembly containing the external source adapter 50 and the collection catheter 40 is coupled to the placed catheter adapter 30. In an alternative embodiment having no collection catheter adapter, the male Luer lock 58 can be configured to screw onto the female hub 29 of the placed catheter 20. As with the female-male Luer lock connection 29, 38 between the placed catheter 20 and the placed catheter adapter 30, other connectors can also be incorporated into the design of the placed catheter adapter 30 and the external source adapter 50.

It is preferable that when two components of the system 10 are coupled together that a tight seal is formed therebetween so that fluid loss and clean-up is kept to a minimum. This is particularly true between the catheters and the adapters, for example between the collection catheter 40 and the distal end 52d of the tube 52 of the external source adapter 50, and between multiple adapters, for example between the proximal end 32p of the tube 32 of the placed catheter adapter 30 and the distal end 52d of the tube 52 of the external source adapter 50. By way of non-limiting example, in one exemplary embodiment a gasket 57 is disposed on the distal end 52d of the tube 52 of the external source adapter 50 and is configured to seal a gap between the distal end 52d of the tube 52 of the external source adapter 50 and the proximal end 32p of the tube 32 of the placed catheter adapter 30. The gasket 57 can help prevent the leakage of fluid as the fluid travels from the collection catheter 40 to the tube 52 of the external source adapter 50. The gasket 57 is preferably made of a flexible and/or compressible material, for example, rubber. In alternative embodiments a gasket can be disposed between any two components of the system 10, and especially between connections where fluid may leak through any gap that exists between two components in communication with each other.

The proximal end 52p of the tube 52 of the external source adapter 50 can be configured to receive a number of different devices, including external sources that are discussed in more detail below. In the illustrated embodiment the proximal end 52p of the tube 52 has a female Luer lock hub 59. The female Luer lock hub 59 allows the proximal end 52p of the tube 52 to receive a male Luer lock of an external source and/or a device for flushing the tube 52 of the external source adapter 50 and the collection catheter 40 with a solution. Two examples of devices for flushing include an intravenous infusion device and a syringe. Further, similar to the placed catheter adapter 30, fluid and/or gases, such as air, can be removed through and/or from the tube 52 of the external source adapter 50 and the collection catheter 40 by using devices for suctioning. While the removal of fluid and/or gases from the tube 52 of the external source adapter 50 and the collection catheter 40 is not as desirable as the removal of fluid from the tube 32 of the placed catheter adapter 30 and the placed catheter 20, it can still be desirable to remove fluid, gases, and other materials from the tube 52 of the external source adapter 50 and the collection catheter 40 prior to use.

While in the illustrated embodiments two adapters are used, the placed catheter adapter 30 and the external source adapter 50, any number of adapters can be used, including one, three, or even more. In fact, no adapters need to be used, as the collection catheter 40 can be disposed directly in the placed catheter 20. However, adapters can help, for example, by allowing for the flow through the collection catheter 40 to be controlled by the valves. It is particularly useful to incorporate tubes into the adapters when the valves are clamps or other devices similar to clamps because some clamps can damage the catheter 40 when the clamps are pinched together.

Figure 3:
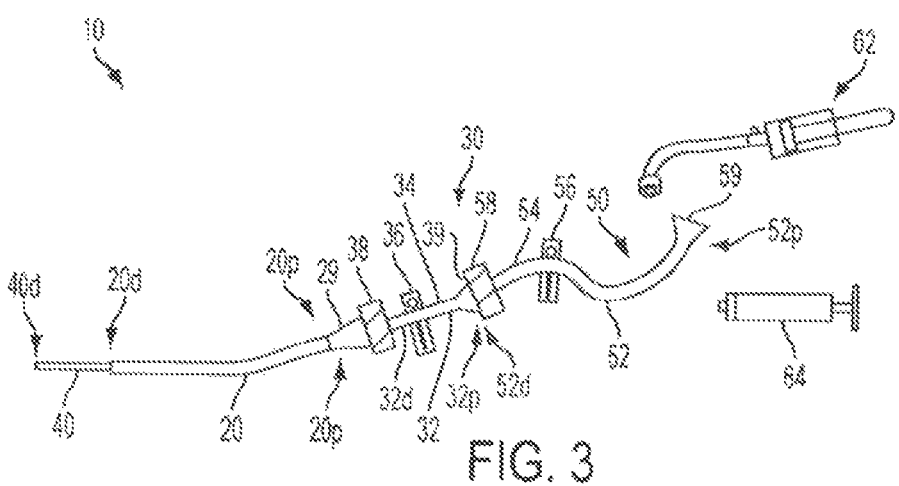
FIG. 3 is a side view of the external source adapter of FIG. 2 coupled to the placed catheter adapter of FIG. 1 to form a system.

An external source, or external sources if more than one is being used either simultaneously or sequentially, can be coupled to the proximal end 52p of the tube 52 of the external source adapter 50. The external source is configured to transport fluid between the body and the external source through the collection catheter 40. As described herein, the external source is configured to remove blood from the body, through the collection catheter 40, and to the external source. Many different types of external sources can be used, depending on the desired use of the external source. Two examples of external sources are illustrated in FIG. 3, a Vacutainer® blood collection tube marketed by BD 62 and a syringe 64. Another example of an external source is discussed above with respect to flushing portions of the system—an intravenous infusion device. A needleless adapter is yet another non-limiting example of an external source. A person skilled in the art will recognize that many other external sources can be used, and the selection of one or more external sources can often depend on the desired use of the system 10. With respect to the Vacutainer® blood collection tube 62 illustrated in FIG. 3, it can be particularly useful for removing blood from a body. The design of the Vacutainer® blood collection tube 62 is such that, once opened, it suctions blood from the body, through the collection catheter 40, and into the Vacutainer® blood collection tube 62. With respect to the syringe 64 illustrated in FIG. 3, it can be particularly useful for performing various tests on blood, although it can also be used for blood removal. Some examples of tests that can be performed using the syringe 64 as the external source include complete blood counts, coagulation studies, serum electrolyte tests, and ionized calcium tests.

The external source can be configured to connect directly to the collection catheter 40, for example in instances where no adapters are used, or it can be configured to connect to a proximal end of the external source adapter 50. In the illustrated embodiment the proximal end 52p of the tube 52 of the external source adapter 50 has the female hub 59, thus making it preferable for the external source to have a male hub. Similar to the connectors of both the placed catheter adapter 30 and the external source adapter 50, while a connector between the proximal end 52p of the tube 52 of the external source adapter 50 and the external source is not necessary, it can make the procedure cleaner and more efficient. Further, although as described above the external source receives fluid from the body, in alternative embodiments the external source can include one or more additional containers coupled to the external source to allow for storage of the removed fluid in some location that is not the external source itself. Such embodiments can allow the external source to be directed only to the transportation of fluid between the body and an outside environment and thus not be limited by a volume capacity.

FIG. 3 illustrates an exemplary embodiment of the assembled system 10 such that the placed catheter adapter 30 is coupled to the placed catheter 20, the collection catheter 40 is disposed in the placed catheter 20, the external source catheter adapter 50 is coupled to both the placed catheter adapter 30 and the collection catheter 40, and the external source adapter 50 is configured to receive one or more external sources, such as the Vacutainer® blood collection tube marketed by BD 62 and the syringe 64. Exemplary methods for combining these components are now described.

In one exemplary embodiment the placed catheter adapter 30 is attached to the placed catheter 20. The placed catheter 20 can already be disposed in the body, or in some embodiments, the method can include positioning the placed catheter 20 near a desired location in the body. As illustrated, the distal end 32d of the tube 32 of the placed catheter adapter 30 is coupled to the proximal end 20p of the placed catheter 20. A connector can be used to facilitate the coupling therebetween, and a variety of different connectors can be used. In the illustrated embodiment the male Luer lock connector 38 of the placed catheter adapter 30 is coupled to the female hub 29 of the placed catheter 20. A valve, or the clamp 36 as illustrated in FIG. 3, of the placed catheter adapter 30 can be opened, if not opened already, and the collection catheter 40 can be inserted into the placed catheter 20. In one embodiment, prior to inserting the collection catheter 40, a flushing device is coupled to the proximal end 32p of the tube 32 of the placed catheter adapter 30 and a solution is run through the tube 32 and the placed catheter 20 to flush the system of any materials and/or fluid. The solution can be any sterile solution, although preferably it is an iso-osmotic solution, such as saline. In another embodiment, prior to inserting the collection catheter 40, a suctioning device is coupled to the proximal end 32p of the tube 32 of the placed catheter adapter 30 and fluid and/or gas, such as air, is suctioned out of the tube 32 and the placed catheter 20 to remove any fluid and/or gas from the system. The collection catheter 40 can be positioned so that the distal end 40d of the collection catheter 40 extends beyond the distal end 20d of the placed catheter 20. As discussed above, the distance that the distal end 40d of the collection catheter 40 extends beyond the distal end 20d of the placed catheter 20 can vary, but in one exemplary embodiment the distal end 40d of the collection catheter 40 extends beyond the distal end 20d of the placed catheter 20 by approximately 1 centimeter. Extending the distal end 40d of the collection catheter 40 beyond the distal end 20d of the placed catheter 20 can reduce the amount of clotting that can typically occur in procedures such as removing blood, extending the life of the intravenous catheter, while enabling a user to obtain blood samples painlessly. It is generally preferred that this method, as well as other methods of a similar nature which are also discussed herein, is performed sterilely to prevent the introduction of microbes into the body.

The external source adapter 50 can be coupled to a proximal end of the collection catheter 40 by a variety of mechanisms and techniques, for example by jamming one component into the other. In one embodiment coupling the external source adapter 50 and the collection catheter 40 occurs prior to inserting the collection catheter 40 into either the tube 32 of the placed catheter adapter 30 or the placed catheter 20, while in another embodiment such coupling occurs after the collection catheter 40 is inserted into at least one of the tube 32 of the placed catheter adapter 30 and the placed catheter 20. Coupling the external source adapter 50 to the collection catheter 40 prior to inserting the collection catheter 40 is preferred when the external source adapter 50 is to be used as the mechanism for coupling the collection catheter 40 to at least one of the placed catheter 20 and the placed catheter adapter 30. Many different mechanisms can be used to place the collection catheter 40 into the placed catheter 20 and couple it to at least one of the placed catheter 20 and the placed catheter adapter 30. By way of non-limiting example, in the illustrated embodiment, the male Luer lock 58 located on the distal end 52*p* of the tube 52 of the external source adapter 50 is configured to mate with the proximal end 32*p* of the tube 32 of the placed catheter adapter 30. The male Luer lock 58 can also be configured to mate with the proximal end 40*p* of the collection catheter 40 in the alternative or in addition to mating with the proximal end 32*p* of the tube 32 of the placed catheter adapter 30. Connecting the male Luer lock 58 to the proximal end 32*p* of the tube 32 of the placed catheter adapter 30 allows the external source adapter 50 to be coupled to the placed catheter adapter 30 with the collection catheter 40 being disposed in the placed catheter 20. Further, a gasket 57 can be placed between any two components of the system 10, for example between the distal end 52*d* of the tube 52 of the external source adapter 50 and the proximal end 32*p* of the tube 32 of the placed catheter adapter 30. The gasket 57 can help keep the amount of fluid loss and the clean-up caused by any gap between the two tubes 32, 52, or any other components between which the gasket 57 is disposed, to a minimum.

Many different external sources, including but not limited to flushing devices and suctioning devices, can be coupled to the proximal end 52*p* of the tube 52 of the external source adapter, for instance at female hub 59. In one embodiment the female hub 59 of the external source adapter 50 can be coupled to a flushing device, which can be operated to run a solution through the tube 52 of the external source adapter 50 and the collection catheter 40 to flush the tube 52 and the collection catheter 40 of any materials. In another embodiment the female hub 59 of the external source adapter 50 can be coupled to a suctioning device, which can be operated to suction fluid and/or gas, such as air, from the tube 52 of the external source adapter 50 and the collection catheter 40. Further, after removal of the flushing device and/or the suctioning device, the female hub 59 of the external source adapter 50 can be coupled to, or configured to receive, one or more external sources, as described in more detail above. In some embodiments, one or more of the external sources are flushing devices and/or suctioning devices, and thus the one or more flushing devices can be used before coupling one or more external sources to the external source adapter 50, after coupling one or more external sources to the external source adapter 50, or can not be used at all.

While the various components of the system 10 can be coupled together in a variety of ways, often depending on the components that are included and excluded from the system, in one exemplary embodiment the placed catheter adapter 30 is coupled to the placed catheter 20, the collection catheter 40 is disposed in both the placed catheter adapter 30 and the placed catheter 20, the external source adapter 50 is coupled to the collection catheter 40 and the placed catheter adapter 30 to allow for fluid to flow from the body, through the collection catheter 40, and into the external source adapter 50, and the external source adapter 50 is coupled to one or more external sources, which can be configured to receive fluid from the external source adapter 50. More specifically, the valve, or clamp 56 as illustrated in FIG. 3, of the external source adapter 50 can be opened, if not opened already, and the external source can be operated to transport fluid between the body and the external source, through the collection catheter 40. Alternatively, the valve can be opened prior to coupling the external source to the proximal end 52*p* of the tube 52 of the external source adapter 50. In one exemplary embodiment, when taking a sample of fluid from the body, a first portion of the sample is not used as part of the sample to make sure that the sample is not compromised, for instance by trapped air. In one embodiment approximately 3 to 5 cubic centimeters of blood are discarded prior to collecting a sample.

After the external source has been operated, the clamp 56 of the external source adapter 50 can be closed and the external source can be removed. Likewise, the external source adapter 50 can be removed from the collection catheter 40, or the combination of the external source adapter 50 and the collection catheter 40 can be removed from the placed catheter adapter 30. Either or both of the external source adapter 50 and the collection catheter 40 can then be disposed of as desired. If further collection is desired, the placed catheter adapter 30 can be left in place so that another collection catheter and/or external source adapter can be coupled thereto. The placed catheter adapter 30 can be left in place for any desired length of time. Once the collection catheter 40 is removed, however, it is generally preferable to close the clamp 36 of the placed catheter adapter 30 so that the exposure of the body to the outside environment is minimized. Alternatively, or in addition to, closing the clamp 36, a cap or other closure device, for example a needless adapter or an injection port, can be placed on the proximal end 32*p* of the tube 32 of the placed catheter adapter 30 or coupled to the female Luer lock hub 39. This not only protects the body from the outside environment, but it can also reduce leakage and/or microbial contamination. In some instances it can be preferable to keep the clamp 36 open once the collection catheter 40 is removed, for example when a continuous intravenous infusion or intermittent medication is desired. Prior to closing the clamp 36, a flushing device or a suctioning device can be coupled to the placed catheter adapter 30 to flush and/or suction the system in a similar manner as described above.

While the illustrated embodiment uses both a placed catheter adapter and an external source adapter, in alternative embodiments zero, one, or more than two adapters can be used. By way of non-limiting example, in an embodiment of a method for transporting a fluid between a body and an external source that does not use any adapters, a collection catheter can be inserted into a placed catheter and positioned so that a distal end of the collection catheter extends beyond a distal end of the placed catheter. A proximal end of the collection catheter can be coupled to an external source, and the external source can be operated to transport fluid between the body and the external source through the collection catheter. The method can also include inserting the placed catheter near a location in the body from which fluid is to be transported, although in some instances the placed catheter may already have been positioned at some earlier point in time prior to inserting the collection catheter. A person skilled in the art would further recognize how to utilize the teachings herein for use with systems or kits that include one or more than two adapters.

Figure 5:
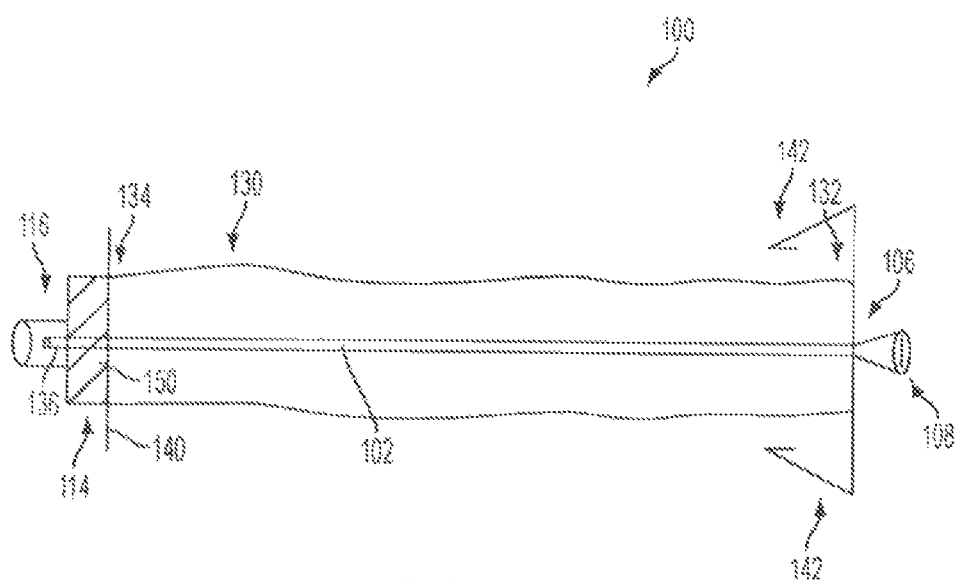
FIG. 5 is a cross-sectional view of one embodiment of a collection catheter system having a protective sheath in an expanded configuration.
Figure 6A:
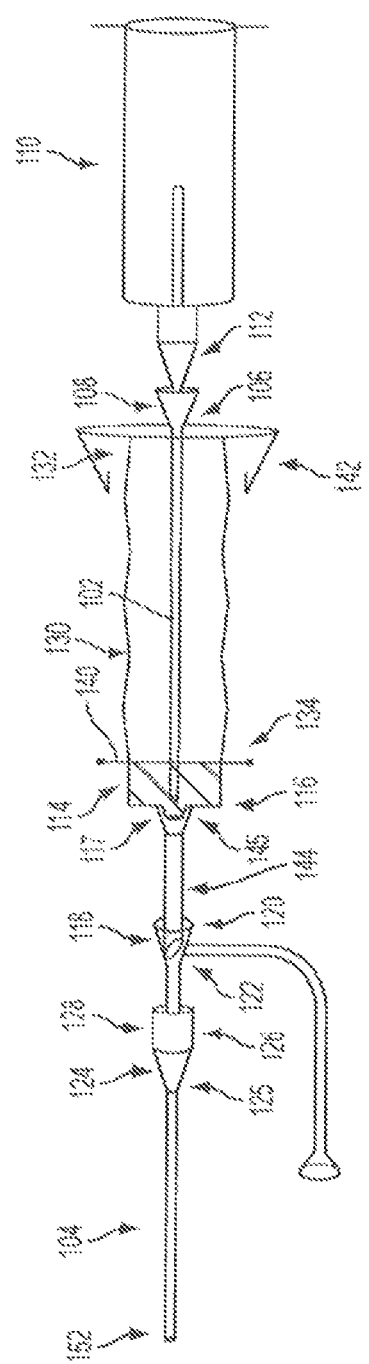
FIG. 6A is a cross-sectional view of the collection catheter system of FIG. 5 being coupled to a placed catheter.
Figure 6B:
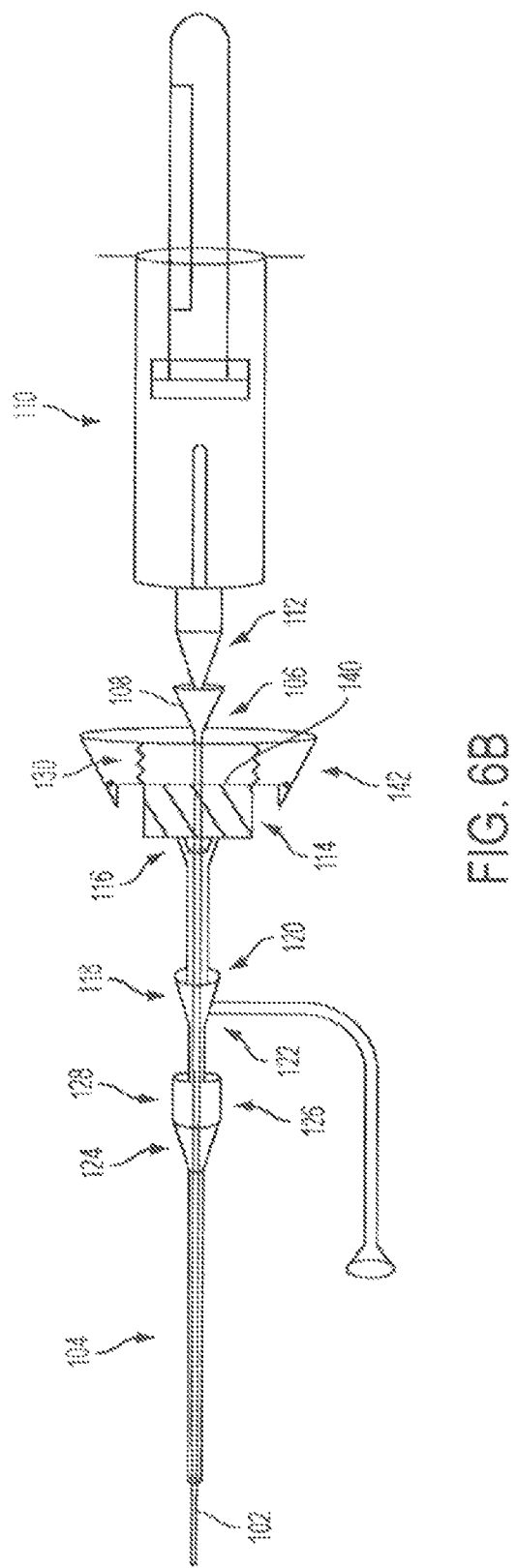
FIG. 6B is a cross-sectional view of the protective sheath of FIG. 5 in a contracted configuration.

Another exemplary embodiment of a collection catheter system 100 is illustrated in FIGS. 5, 6A, and 6B. The collection catheter system 100 can include a collection catheter 102 that is configured to be used with any of the conduits and/or placed catheters described herein. In the illustrated embodiment however, the collection catheter 102 is configured to be used with a placed catheter 104 illustrated in FIGS. 6A and 6B. The collection catheter 102 can generally be elongate and tubular, and can have a proximal end 106 and a distal end 136. The placed catheter 104 can also be elongate and tubular with a proximal end 125 and a distal end 152. As with the embodiments described above, the collection catheter 102 and the placed catheter 104 can have similar shapes such that the placed catheter 104 can receive the collection catheter 102 therein. The catheters 102, 104 can each have a length that enables the distal end 136 of the catheter 102 to extend a distance beyond the distal end 152 of the placed catheter 104 when inserted therethrough.

In some embodiments, the collection catheter 102 can have a connector disposed on its proximal end 106 that is configured to couple to a corresponding connector disposed on an external source. For example, the collection catheter 102 can have a female Luer lock hub 108 disposed thereon configured to couple to a male Luer lock 112 of an external source 110, as shown in FIGS. 6A and 6B. As will be appreciated by those skilled in the art, the external source 110 can be any suitable external source such as a syringe, vacutainer barrel, and/or any other source disclosed herein or known in the art.

The collection catheter system 100 can also have a connector disposed on its distal end 114 generally configured to couple to a corresponding connector on the placed catheter 104, and/or on a saline lock or other adapter component coupled to the placed catheter 104. In the illustrated embodiment, a male Luer lock 116 is disposed on the distal end 114 of the collection catheter system 100 and is configured to couple to a corresponding female Luer lock hub 118 disposed on a proximal end 120 of a saline lock 122 disposed within the placed catheter 104. As will be appreciated by those skilled in the art, the collection catheter system 100 can couple to any saline lock known in the art, including any described herein, and/or can couple directly to the placed catheter 104. In the illustrated embodiment, however, the saline lock 122 includes a male Luer lock 126 on its distal end 128 that can couple to a female Luer lock hub 124 of the placed catheter 104.

The collection catheter system 100 can also include a sterile protective element that is configured to sterilely enclose the catheter 102 until use. When the catheter system 100 is ready to be used, the protective element can be collapsible and/or contractible so that the catheter 102 is exposed and can be utilized, as will be described below. In the illustrated embodiment, a substantially flexible protective sheath 130 is provided as the protective element. The protective sheath 130 can be generally elongate and tubular, and can have a proximal end 132 and a distal end 134. The protective sheath 130 can have a length sufficient to substantially enclose the length of the catheter 102 in its expanded configuration. The protective sheath 130 can generally be flexible so that it is collapsible and/or contractible, and it can be formed from any suitable material known in the art, including, but not limited to polymeric materials and fabrics that are biocompatible and used in a variety of medical procedures. The proximal end 132 of the protective sheath 130 can be substantially fixedly and/or rigidly coupled to the proximal end 106 of the catheter 102. The two proximal ends 132, 106 can be fixed together by any fixation mechanism known in the art, including interference fit, press fit, adhesive, fastener, etc. The distal end 134 of the protective sheath 130 can be substantially fixedly attached to a proximal end 150 of the male lock 116 such that the distal end 134 of the protective sheath 130 can move relative to the catheter 102.

As shown in FIGS. 6A and 6B, the protective sheath 130 can be configurable and/or movable between two configurations. In an expanded configuration, shown in FIGS. 5 and 6A, the protective sheath 130 is expanded to its substantially full length and can circumferentially surround and enclose a length of the catheter 102 such that only the distal end 136 of the catheter 102 extends beyond the distal end 134 of the protective sheath 130. In some embodiments, the protective sheath 130 can surround substantially the entire length of the catheter 102, including its distal end 136. In the expanded configuration, the catheter system 100 can be stored, transported, etc. because the catheter 102 is enclosed within a sterile environment. In addition, the catheter system 100 can be coupled to the placed catheter 104 while the protective sheath 130 is in the expanded configuration.

Once the catheter system 100 is coupled to the placed catheter 104, whether directly or through the saline lock 122, the protective sheath 130 can be moved to a collapsed and/or contracted configuration, thereby moving the catheter 102 through the placed catheter 104. The flexibility of the protective sheath 130 can allow the material to bunch together like a bellows so that the length of the protective sheath 130 is shortened, as shown in FIG. 6B. In the contracted configuration, the protective sheath 130 only encloses a portion of a length of the catheter 102, because the catheter 102 extends through the placed catheter 104, as will be described in more detail below. In addition, a latch mechanism can be associated with the protective sheath 130 to retain it in the contracted configuration. In the illustrated embodiment, a lip 140 is disposed on the distal end 134 of the protective sheath 130, and one or more clips 142 can be disposed on the proximal end 132 of the protective sheath 130. The clips 142 can expand to engage and clasp the lip 140 when the protective sheath 130 is in the contracted configuration and thus retain the protective sheath 130 in the contracted configuration. As will be appreciated by those skilled in the art, any suitable latch mechanism known in the art can be used to retain the protective sheath 130 in the contracted configuration.

In use, in one embodiment, the collection catheter system 100 can be coupled to the placed catheter 104 while the protective sheath 130 is in the expanded configuration. If a saline lock having a resealable membrane is being utilized with the placed catheter 104, a needle can be inserted to pierce the membrane and withdrawn before coupling the collection catheter system 100 thereto. In other embodiments, a hollow needle 144 can be coupled to the male lock 116 on the collection catheter system 100 and can be used to pierce the resealable membrane of a saline lock, as shown in FIG. 6A. The female hub 118 on the saline lock 122 can then be coupled to a male Luer lock 117 on a distal end 145 of the needle 144. In addition, the male lock 112 on the external source 110 can be coupled to the female hub 108 on the collection catheter system 100 in preparation for retrieving a sample through the collection catheter system 100.

Once the couplings are secure, the proximal end 132 of the protective sheath 130 can be moved by a user distally toward the distal end 134 thereof, collapsing the protective sheath 130 to a smaller length. Movement of the proximal end 132 of the protective sheath 130 distally moves the catheter 102 distally through the needle 144, if utilized, through the saline lock 122, and through the catheter 104. The catheter 102 is moved distally until the distal end 136 of the catheter 102 extends a distance beyond the distal end 152 of the placed catheter 104.

Once the distal end 136 of the catheter 102 extends a distance beyond the distal end 152 of the placed catheter 104, the protective sheath 130 is in its contracted configuration, and the clips 142 can be latched to the lip 140 to retain the protective sheath 130 in this configuration. The external source 110 can then be actuated to transfer fluid from the body, through the catheter 102, and to the external source 110. Once complete, the clips 142 can be unlatched from the lip 140, and the proximal end 132 of the protective sheath 130 can be moved proximally to expand the protective sheath 130 and to withdraw the catheter 102 from the placed catheter 104. Once the catheter 102 is fully withdrawn, the collection catheter system 100 can be uncoupled from the saline lock 122 and/or the placed catheter 104 and can be disposed of. The placed catheter 104 can then be flushed with saline using the saline lock 122.

Figure 7:
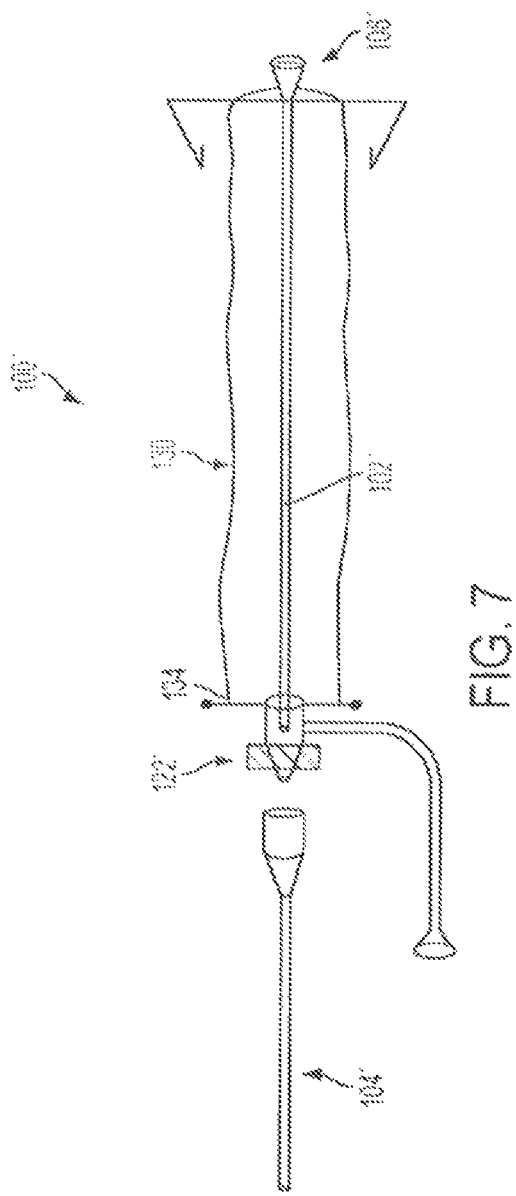
FIG. 7 is a cross-sectional view of another embodiment of a reusable collection catheter system.

In some embodiments, a collection catheter system can be reusable rather than disposable. For example, as shown in FIG. 7, a collection catheter system 100' is provided having substantially similar components to the embodiment shown in FIGS. 5, 6A, and 6B. In this reusable embodiment, however, a saline lock 122' is disposed on a distal end 134' of a protective sheath 130'. The saline lock 122' can be coupled to the placed catheter 104, and the collection catheter system 100' can be disposed there permanently and/or for as long as necessary for repeated uses. When a sample is required, an external source can be coupled to a female hub 108' on a catheter 102', and the protective sheath 130' can be collapsed and/or contracted as described above to move the catheter 102' through the placed catheter 104' to obtain the sample. Once complete, the protective member 130' can be expanded again to withdraw the catheter 102' from the placed catheter 104'. The external source can be removed and the system 100' and the placed catheter 104 can be flushed with saline in preparation for another use.

As will be appreciated by those skilled in the art, any of the components described herein can be interchangeable with one another. For example, any of the adapters, external sources, connectors, catheters, valves, etc. shown in FIGS. 1-3 can be used with any of the embodiments described in FIGS. 5-7 and vice-versa. Further, any of the components described herein can be included in a kit and can be disposable or reusable as needed.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for transporting a fluid between a body and an external source, comprising:
   a catheter having a proximal and a distal send, wherein the catheter is configured to:
     fit inside a conduit disposed in a body;
     extend such that the distal end extends beyond a distal end of the conduit disposed in the body; and
     fluidically couple to an external source at the proximal end to allow a fluid to be transported between the external source and the body; and
   a protective sheath extending between the proximal end of the catheter and a catheter connector, the protective sheath being movable between an expanded configuration in which the catheter is substantially enclosed by the protective sheath, and a contracted configuration in which only a proximal portion of the catheter is enclosed by the protective sheath and the distal end of the catheter extends a distance beyond a distal end of a conduit.

2. The system of claim 1, further comprising:
   a tube having a distal end coupled to the proximal end of the catheter and a proximal end configured to couple to the external source; and
   a valve configured to open and close a pathway of the tube.

3. The system of claim 2, further comprising:
   a connector coupled to the distal end of the tube and configured to couple to a conduit disposed in a body.

4. The system of claim 2, further comprising:
   a conduit device adapter, comprising:
   a device adapting tube having a distal end configured to fluidically couple to a conduit disposed in a body and a proximal end configured to couple to the distal end of the tube; and
   a device adapting valve configured to open and close a pathway of the device adapting tube.

5. The system of claim 4, further comprising:
   a first connector fluidically coupled to the distal end of the tube and configured to couple to the proximal end of the device adapting tube; and
   a second connector fluidically coupled to the distal end of the device adapting tube and configured to fluidically couple to a conduit disposed in a body.

6. The system of claim 5, further comprising:
   a second catheter, wherein the second catheter is the conduit disposed in a body.

7. The system of claim 1, wherein the catheter connector is configured to couple to a conduit connector disposed on a proximal end of a conduit.

8. The system of claim 1, wherein the protective sheath includes a latch mechanism configured to retain the protective sheath in the contracted configuration when actuated.

9. The system of claim 1, wherein the catheter is permanently coupled to a conduit.

* * * * *